United States Patent [19]

Schaefer et al.

[11] Patent Number: 4,891,166

[45] Date of Patent: Jan. 2, 1990

[54] DIQUATERNARY POLYSILOXANES, THEIR SYNTHESIS AND USE IN COSMETIC PREPARATIONS

[75] Inventors: Dietmar Schaefer; Manfred Krakenberg, both of, Essen, Fed. Rep. of Germany

[73] Assignee: Th. Goldschmidt AG, Essen, Fed. Rep. of Germany

[21] Appl. No.: 348,089

[22] Filed: May 3, 1989

Related U.S. Application Data

[63] Continuation-in-part of Ser. No. 193,409, May 12, 1988, abandoned.

[30] Foreign Application Priority Data

Jun. 6, 1987 [DE] Fed. Rep. of Germany ....... 3719086

[51] Int. Cl.⁴ .............................................. C07F 7/10
[52] U.S. Cl. ................................ 260/404.5; 556/418; 556/419; 556/425
[58] Field of Search ................ 556/418, 419, 425; 260/404.5

[56] References Cited

U.S. PATENT DOCUMENTS 4,005,024 1/1977 Rodriguez et al. ................. 556/418
4,185,087 1/1980 Morlino .

FOREIGN PATENT DOCUMENTS 0017121 10/1980 European Pat. Off. ............ 556/419
1493384 3/1971 Fed. Rep. of Germany .

OTHER PUBLICATIONS

Chemie und Technologie der Silicone (Chemistry and Technology of the Silicones) p. 536, 2nd Edition, by Walter Noll, Verlag Chemie.

*Primary Examiner*—Joseph L. Schofer
*Assistant Examiner*—Jeffrey T. Smith
*Attorney, Agent, or Firm*—Toren, McGeady & Associates

[57] ABSTRACT

Compounds of the general formula

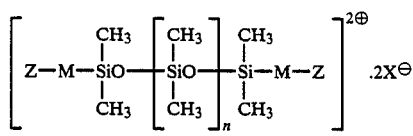

are disclosed in which Z is

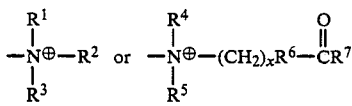

$R^1$, $R^2$, $R^3$ are alkyl groups with 1 to 22 carbon atoms or alkenyl groups with 2 to 22 carbon atoms, at least one of the $R^1$, $R^2$ or $R^3$ groups having at least 10 carbon atoms, $R^4$, $R^5$, $R^7$ are alkyl groups with 1 to 22 carbon atoms or alkenyl groups with 2 to 22 carbon atoms, $R^6$ is —O— or the $NR^8$ group, $R^8$ being an alkyl or hydroxyalkyl group with 1 to 4 carbon atoms or a hydrogen group, x is 2 to 4, M is a bivalent hydrocarbon group with at least 4 carbon atoms, which has a hydroxyl group and may be interrupted by an oxygen atom, n is a number from 0 to 200, and $X^\ominus$ is an inorganic or organic anion.

The compounds can be prepared by reacting compounds of the general formula

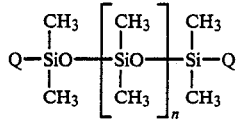

in which Q is a hydrocarbon group with at least 4 carbon atoms, which has an epoxide group and may be interrupted by an oxygen atom, and n is as defined above, with tertiary amines of the general formula

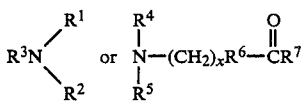

in which $R^1$, $R^2$, $R^3$, $R^4$, $R^5$, $R^6$, $R^7$ and x are defined as above, in such quantitative ratios that at least one tertiary amino group corresponds to each epoxide group. The reaction is carried out in the presence of one acid equivalent or HX, based on the nitrogen atom to be quaternized, and at temperatures of 40° to 120° C.

The compounds are useful in cosmetic preparations, especially in preparations for the care of the hair. They improve the combability of the hair and, at the same time, improve the gloss and give permanence to the hairstyle.

11 Claims, No Drawings

DIQUATERNARY POLYSILOXANES, THEIR SYNTHESIS AND USE IN COSMETIC PREPARATIONS

This is a continuation-in-part of application Ser. No. 193,409, filed May 12, 1988 now abandoned.

FIELD OF THE INVENTION

The present invention relates generally to novel diquaternary polysiloxanes, whose quaternary nitrogen groups are terminally linked to the polysiloxane molecule and to compositions containing such compounds.

Considered from another aspect, the present invention is concerned with the synthesis of such compounds, as well as with their use in cosmetic preparations, especially in preparations for the care of the hair.

BACKGROUND INFORMATION AND PRIOR ART

The use of organopolysiloxanes for the preparation of hair tonics and other hair care preparations is well known. In "Chemie und Technologie der Silicone" (Chemistry and Technology of the Silicones), by Walter Noll, Verlag Chemie, 2nd Edition, 1968, page 536, however, it is stated that the objective of maintaining the hairdo independent of the effects of moisture cannot be accomplished with normal polydimethylsiloxanols. Rather, the silicone must be fixed on the hair with the help of functional groups.

German Auslegeschrift 14 93 384 discloses organosiloxane compounds or compound mixtures of the formula

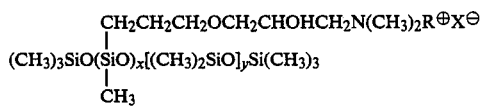

in which R represents hydrogen or $CH_3$, X is halogen and $x=1$ to 10 and $y=0$ to 8.5, y:x not being larger than 8.5:1.

These organosiloxanes with quaternary ammonium groups can be synthesized by reacting epoxysiloxanes of the formula

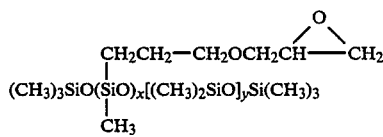

in a known manner with dimethylamine and converting the resulting dimethylaminoorganosiloxane of formula

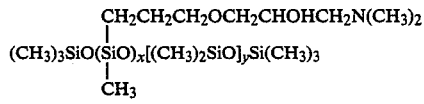

in a known manner with a hydrogen halide or with a methyl halide into the quaternary ammonium compound of the aforementioned formula.

According to U.S. Pat. No. 4,185,087, the aforementioned organopolysiloxanes with quaternary ammonium groups can be used for hair care preparations. It is stated in the patent that while simple, aqueous shampoos can release dirt and remove an excess of fat from the hair, most shampoos however remove fat so thoroughly from the hair that damage to the hair can be observed. The patent asserts that after being washed, the hair becomes electrostatically charged and therefore difficult to comb.

The patent also teaches that the addition of lanolin derivatives, glycol, fatty acid esters or proteins improves the manageability of the hair after washing. At the same time, however, the additions interfere with foaming during washing. The hair, pursuant to the patent, becomes somewhat sticky and does not feel natural.

According to U.S. Pat. No. 4,185,087, the previously described organopolysiloxanes with quaternary groups are said to eliminate these disadvantages and to improve the combability of the washed hair, the permanence of the hairstyle and the gloss of the hair.

The starting materials for the preparation of the compounds described in the German Auslegeschrift 14 93 384 are the corresponding methylhydrogenpolysiloxanes. These generally are equilibrated mixtures, that is, siloxane mixtures in which the number of methylhydrogensiloxy and dimethylsiloxy units corresponds to a random (statistical) distribution. Therefore, in siloxanes in which x has a low value, the proportion of such siloxanes in which $x=0$ cannot be disregarded. This means in turn that a proportion of unmodified silicone oils is unavoidably present in products of this method. This proportion, however, does not contribute to improving the ability of combing the hair or to improving the hairdo or the gloss of the hair.

It is a further disadvantage of the compounds described in German Auslegeschrift 14 93 384 that the dimethylsiloxy chains are always interrupted by methylsiloxy groups which have lateral quaternary nitrogen groups. The typical siloxane character which is desirable for improving the properties of the hair is, however, based particularly on the presence of dimethylsiloxy chains. The optimum ability to comb the hair and the optimum gloss are therefore not assured.

Similar teachings arise out of European Patent No. 0,017,121 (corresponding to German Offenlegungsschrift 2 912 485). Here also, organopolysiloxanes with quaternary ammonium groups are described in shampoos and hair care preparations to improve the properties of the hair. The compounds correspond to the general formula

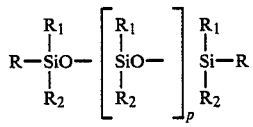

in which $R_1$ and $R_2$ represent alkyl groups with 1 to 4 carbon atoms or an aryl group, p represents the numbers from 0 to 50 and R the

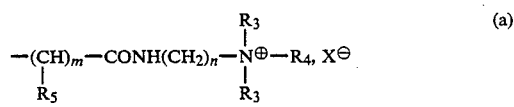

group or the

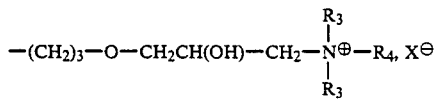

group, in which $R_3$ is an alkyl or hydroxyalkyl group with 1 to 3 carbon atoms, $R_4$ is $R_3$ or aryl-$CH_2$- or the allyl group, $R_5$ is hydrogen or methyl, $X^\ominus$ represents the anions $Cl^\ominus$, $Br^\ominus$, $I^\ominus$, $CH_3SO_4^\ominus$ or $C_2H_5SO_4^\ominus$, m represents numbers from 2 to 10 and n the numbers from 2 to 4.

The compounds which are described in European Patent No. 0,017,121 are also not totally satisfactory when used in preparations for the care of the hair. For example, the combability of hair which has been treated with the compounds of the European patent is not yet adequate. This is observed especially when the molecular weight of these compounds is low for small values of p. The compounds can then also be washed out easily. Moreover, in the event of decomposition of these compounds, for example, a thermal decomposition, amines are released, the alkyl groups of which have a low molecular weight. These amines have an unpleasant odor.

OBJECT OF THE INVENTION

It is the primary object of the present invention to provide novel diquaternary polysiloxanes which have improved application properties and are particularly useful in hair care preparations.

It is also an object to provide a simple method for the synthesis of the novel compounds.

Generally, it is an object of the invention to improve on the art of hair cosmetics.

SUMMARY OF THE INVENTION

Surprisingly, it has been ascertained that the desirable profile of properties is to be found in new compounds of the general formula

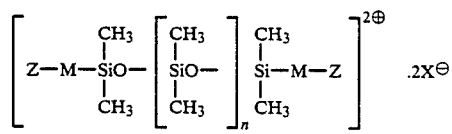

wherein Z is the

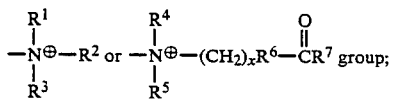

$R^1$, $R^2$, $R^3$ are alkyl groups with 1 to 22 carbon atoms or alkenyl groups with 2 to 22 carbon atoms, at least one of the $R^1$, $R^2$ or $R^3$ groups having at least 10 carbon atoms;

$R^4$, $R^5$, $R^7$ are alkyl groups with 1 to 22 carbon atoms or alkenyl groups with 2 to 22 carbon atoms; p1 $R^6$ is —O— or the $NR^8$ group, $R^8$ being an alkyl or hydroxyalkyl group with 1 to 4 carbon atoms or a hydrogen group;

x is 2 to 4;

M is a bivalent hydrocarbon group with at least 4 carbon atoms, which has a hydroxyl group and may be interrupted by an oxygen atom;

n is a number from 1 to 200, and $X^\ominus$ is an inorganic or organic anion.

The $R^1$, $R^2$ and $R^3$ groups as well as the $R^4$, $R^5$ and $R^7$ groups may be the same or different in the molecule. Compounds in which two of the $R^1$, $R^2$ and $R^3$ groups are lower alkyl groups with 1 to 4 carbon atoms and the remaining third group is a long-chain hydrocarbon group with at least 10 carbon atoms are preferred. Especially the saturated and unsaturated hydrocarbon groups which are derived from the naturally occurring fatty acids are preferred as long-chain hydrocarbon groups.

If the $R^4$, $R^5$ and $R^7$ groups are next to one another, then those compounds are preferred, in which $R^4$ and $R^5$ represent lower hydrocarbon groups with 1 to 4 carbon atoms and the $R^7$ group is derived from an $R^7COOH$ fatty acid, which has at least 8 carbon atoms.

Within the compounds of the invention, the two Z groups may have the same or a different meaning.

M is a bivalent hydrocarbon group with at least 4 carbon atoms, which has a hydroxyl group and may be interrupted by an oxygen atom. The following groups are preferred:

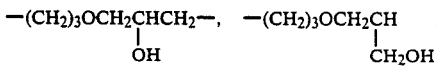

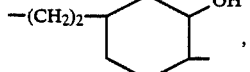 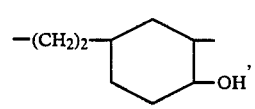

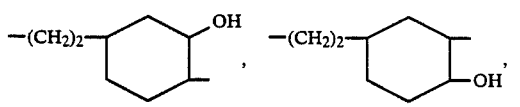

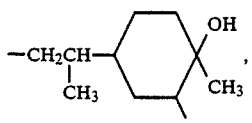

Examples of further M groups are

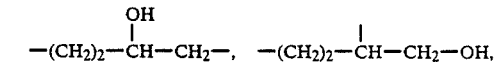

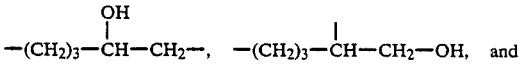

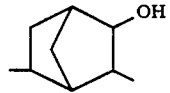 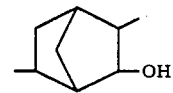

The subscript n is a number from 1 to 200. For higher value of n, the conditions of synthesis are such that the compounds are present in the form of mixtures in which n is then to be understood as an average value.

$X^\ominus$ is an inorganic or organic anion. When the new polymers of the invention are used as a component of hair tonics or the like hair care preparations, care must be taken to ensure that the anion originates from a physiologically tolerated acid. Examples of suitable anions are acetate, chloride, bromide, hydrogen sulfate and sulfate ions.

If the quaternary nitrogen blocks or groups are represented by the letter A and the polysiloxane blocks by the letter B, the polymeric compounds of the invention have the structure ABA.

Examples of diquaternary siloxanes of the invention are:

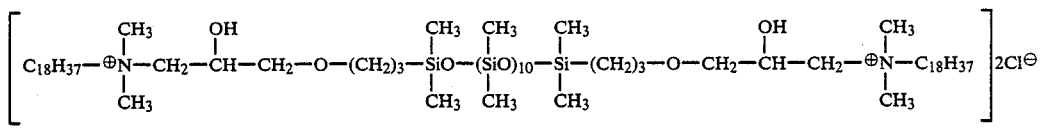

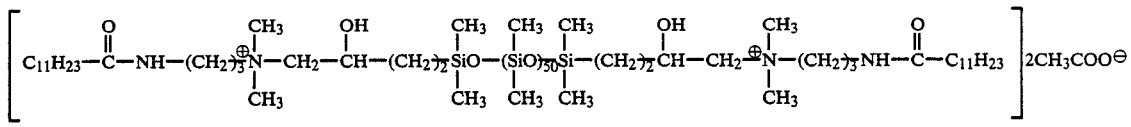

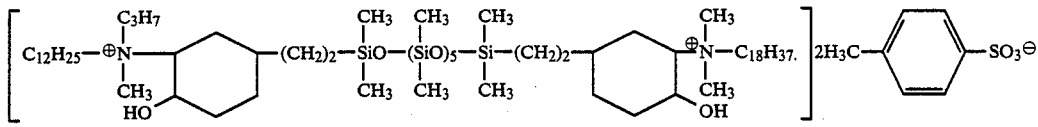

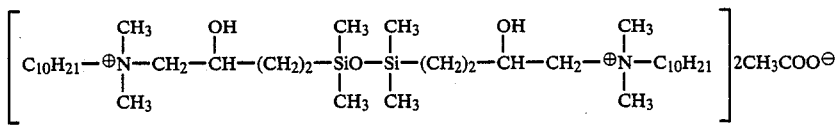

The products of the invention are viscous to highly viscous, oily to pasty, colorless to slightly yellow or reddish products. The solubility of the polymers of the invention is determined by the ratio of dimethylsiloxy units to the number of quaternary ammonium groups and by the molecular weight of the compounds.

For use in cosmetics, especially in hair care preparations, products are generally preferred which are soluble or dispersible in water or water-miscible auxiliary solvents, such as monohydric or multihydric alcohols.

The synthesis of the new compounds is accomplished in a manner analogous to that of the state of the art. The method is characterized in that compounds of the general formula

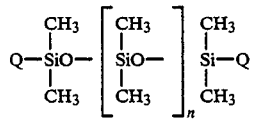 II in which
Q is a hydrocarbon group with at least 4 carbon atoms, which has an
epoxide group and may be interrupted by an oxygen atom and
n is as defined above,
are reacted in a known manner with tertiary amines of the general formula

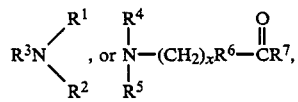 Ia in which $R^1$, $R^2$, $R^3$, $R^4$, $R^5$, $R^6$, $R^7$ and x are defined as above, in such quantitative ratios, that at least one tertiary amino group corresponds to each expoxide group and that the reaction is carried out in the presence of one acid equivalent HX, based on the nitrogen atom, which is to be quaternized, and at temperatures of 40° to 120° C.

Q is a hydrocarbon group with at least 4 carbon atoms which has an epoxide group and may be interrupted by an oxygen atom. Preferred examples of such Q groups are:

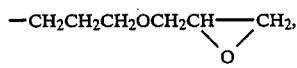

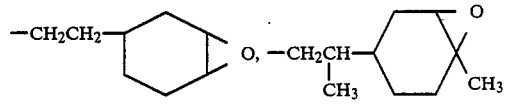

The subscript n has the meaning stated above.

The polysiloxanes with terminal epoxide groups of Formula II are reacted with the aforementioned tertiary amines in a known manner. The reaction is carried out in the presence of an acid equivalent HX, based on the nitrogen atom which is to be quaternized. In so doing, the quantity ratios maintained are such that at least one tertiary amino group corresponds to each Q group of compound II. The reaction is preferably carried out in an aqueous or aqueous/alcoholic solution. To accelerate it, the reaction is advantageously conducted at elevated temperatures, the maximum reaction temperature generally being determined by the reflux temperature of the solvent. A reaction temperature of 40° to 120° C. is therefore preferred.

The invention is also concerned with the use of compounds of the invention in cosmetics, especially, as stated, in preparations for the care of hair. The compounds of the invention have the required combination of properties which was listed at the beginning. The desired properties of the hair care preparations are obtained if an effective amount is added to the preparation. An effective amount is between about 0.2 to 5% by weight.

Methods for producing the compounds of the invention and the properties of these compounds are described in greater detail in the following examples, it being understood that these Examples are given by way of illustration and not by way of limitation.

EXAMPLE 1

Synthesis of a diquaternary polysiloxane of the invention of the general formula

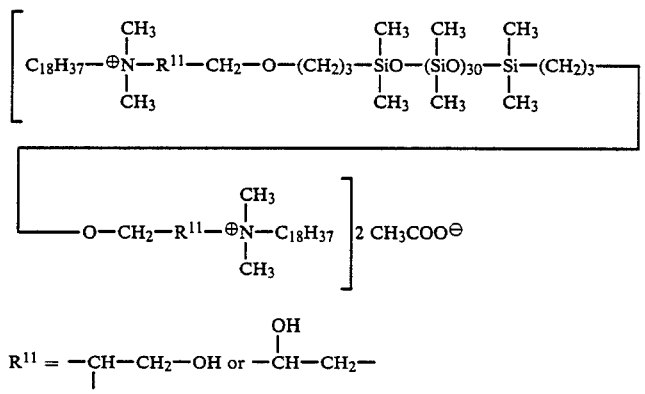

To a 1 L 4-neck flask, equipped with stirrer, dropping funnel, thermometer and reflux condenser, 59.4 g (0.2 moles) of stearyldimethylamine and 80 g of water are added and mixed at 20° C. with 12 g (0.2 moles) of acetic acid.

After 30 minutes, the temperature is raised to 50° C., after which 258.2 g (0.1 mole) of an epoxysiloxane of the general formula

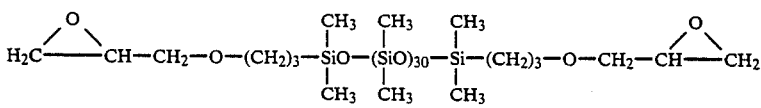

is added dropwise. After the addition of 200 mL of isopropanol, the temperature is raised to the refluxing temperature and the mixture is stirred for 6 hours. The water/isopropanol mixture is distilled off at 100° C. and 0.2 bar.

Yield: 325 g of diquaternary polysiloxane; yellow to reddish product, highly viscous at room temperature.

Quaternary nitrogen found: 0.8%; theoretical: 0.8%

EXAMPLE 2

Synthesis of a diquaternary polysiloxane of the invention of the general formula

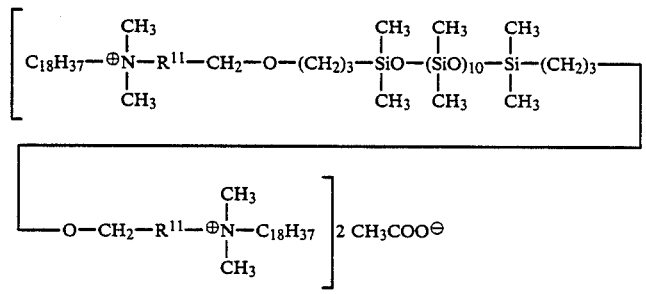

The procedure is the same as that described in Example 1, an epoxysiloxane being used, in which n has a value of 10.

| Formulation: | |
|---|---|
| stearyldimethylamine: | 59.4 g (0.2 moles) |
| acetic acid: | 12.0 g (0.2 moles) |
| epoxysiloxane*: | 110.2 g (0.1 moles) |
| water: | 80 g |
| isopropanol: | 200 g |

*epoxysiloxane of the general formula:

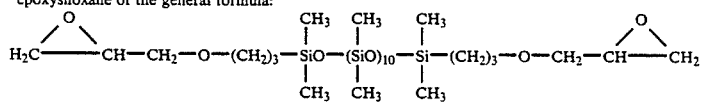

Yield: 176 g of diquaternary polysiloxane; yellow to reddish product, highly viscous at room temperature.

Quaternary nitrogen found 1.4%; theoretical: 1.5%.

EXAMPLE 3

Synthesis of a diquaternary polysiloxane of the invention of the general formula

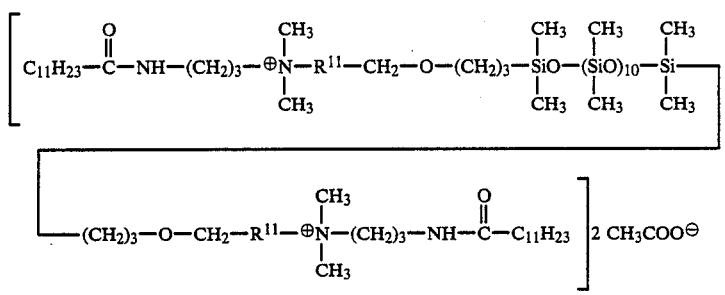

The procedure is the same as that described in Example 1; however, lauryl (dimethylaminopropyl)amide is used instead of stearyldimethylamine and the epoxysiloxane is the one from Example 2 with $n=10$.

Formulation:
lauryl (dimethylaminopropyl)amide: 56.8 g (0.2 moles)
acetic acid: 12.0 g (0.2 moles)
epoxysiloxane from Example 2: 110.2 g (0.1 moles)
water: 80 g
isopropanol: 200 g Yield: 174 g of diquaternary polysiloxane, yellow to reddish product, highly viscous at room temperature. Quaternary nitrogen found 1.5%; theoretical 1.6%.

EXAMPLE 4

Preparation and evaluation of the hair treatment agents using the diquaternary polysiloxane (percentages are by weight) synthesized in Examples 1 to 3.

| | Conditioning Shampoo | |
|---|---|---|
| A | Tego(R) betaine L7[1]: | 2% |
| | Antil(R) 141 liquid[2]: | 3% |
| B | Si quat from Example 1: | 2% |
| | 1,2-propylene glycol: | 4% |
| C | sodium lauryl ether sulfate: | 10% |
| D | water: | 79% |

For the preparation, the components were added in the sequence given (A to D). Each mixture had to be in the form of a clear solution before the addition of further components.

| Cream Rinse I | | | Cream Rinse II | | |
|---|---|---|---|---|---|
| A | Teginacid (R)X[3]: | 6% | A | Teginacid (R)(R)X[3]: | 6% |
| | cetyl alcohol: | 0.5% | | cetyl alcohol: | 0.5% |
| B | Si quat from Example 2: | 2% | B | Si quat from Example 3: | 2% |
| | water: | 91.5% | | water: | 91.5% |

In a practical application in a side-by-side comparison test on human hair, (one half of the hair with inventive product and the other half prior art product) the ability to comb the wet or dry hair was better and the gloss was improved in comparison with shampoo formulations or cream rinses with quaternary siloxanes of the state of the art and conditioning shampoos and cream rinses on the market which are based on a strictly organic quat.

EXAMPLE 5

Two investigations were conducted. The first investigation is directed to the hydrolysis stability of the inventive compounds as compared to those of compounds disclosed in European Patent 0017121 to Petzold. The second investigation concerns a comparison of the application technical properties of such compounds.

Test of Hydrolysis Stability

Diquaternary siloxanes of the following structure were tested:

$$\left[ R-\overset{\oplus}{N}(CH_3)_2-M-(Si(CH_3)_2-O-)_{11}Si(CH_3)_2-M-\overset{\oplus}{N}(CH_3)_2-R \right] 2\, CH_3OO^{\ominus}$$

$$M = -(CH_2)_3-O-CH_2-\underset{OH}{CH}-CH_2- \text{ or}$$

$$-(CH_2)_3-O-CH_2-CH-CH_2-OH$$

Siloxane A: $R = C_{11}H_{23}-NHC(=O)-(CH_2-)_3$  Of the invention

Siloxane B: $R = C_{18}H_{37}$  Of the invention

Siloxane C: $R = CH_3-CH(CH_3)-$  Not of the invention (Petzold)

Siloxane D: $R = CH_3$  Not of the invention (Petzold)

For the purpose of testing the hydrolysis stability of the above-indicated siloxanes, the following procedure was adopted. An aqueous solution of each of the siloxanes of a concentration of 1% by weight was stored at 60° C. and the quaternary nitrogen content of the solution was determined immediately as well as after 7 days storage. This was accomplished by potentiometric titration.

TABLE

| | Results | |
|---|---|---|
| | Quaternary Nitrogen (%) | |
| Siloxane | Starting Value | After 7 Days |
| A | 0.015 | 0.015 |
| B | 0.014 | 0.014 |
| C | 0.019 | 0.007 |

TABLE-continued

| | Results | |
|---|---|---|
| | Quaternary Nitrogen (%) | |
| Siloxane | Starting Value | After 7 Days |
| D | 0.021 | 0.008 |

The table clearly indicates that the content of quaternary nitrogen in the solution remains constant in the inventive compounds. In other words, no measurable hydrolysis sets in. By contrast, in the solutions of the Petzold compounds, the content of quaternary nitrogen decreases significantly upon storage. This decrease is a consequence of the hydrolysis of the compounds. It can be reasonably assumed that the hydrolysis of the compounds takes place at the places indicated by arrows in the following formula:

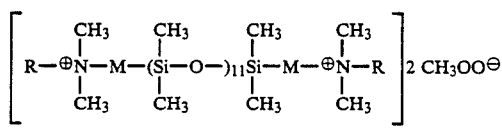

Test in Respect of Hair—Cosmetic Properties

With a view to determining the hair—cosmetic properties, creme rinses were prepared with the inventive compounds and compounds of Petzold. Hair treated with the respective rinses were then compared in respect to their characteristics. For this purpose, again, siloxanes A, B, C and D, as defined above, were used. The creme rinse preparations had the following composition:

| | | Cream Rinses | | | |
|---|---|---|---|---|---|
| | | I | II | III | IV |
| A | Teginacid ® X: | 6% | 6% | 6% | 6% |
| | Cetylalcohol: | 0.5% | 0.5% | 0.5% | 0.5% |
| B | Diquaternary Siloxane | 2% A | 2% B | 2% C | 2% D |
| | Water | 91.5% | 91.5% | 91.5% | 91.5% |

To prepare the respective creme rinse, components A were mixed together with components B and the mixture was homogenized at 60° C. whereupon the product was cooled under agitation.

As in Example IV, the creme rinses were tested on human hair in a "side-by-side" comparison test in which one half of the hair was treated with the inventive product and the other half with the comparison prior art product. Tests on ten different heads were carried out. The average values of the tests are tabulated below.

TABLE

| | I/III | II/IV |
|---|---|---|
| Combability (Wet Hair) | 1.7/2.0 | 1.6/2.1 |
| Combability (Dry Hair) | 1.4/1.9 | 1.2/2.0 |
| Feel or Handle (Wet) | 1.5/2.1 | 1.3/2.3 |
| Fee or Handle (Dry) | 1.3/1.8 | 1.3/2.0 |
| Shine of Dry Hair | 1.7/1.7 | 1.8/2.2 |
| Increase in Heaviness of the Hair (*) | 2.0/2.6 | 2.1/2.6 |

(*) Grading: 1 = low ... 5 = high

In the above table, except for the last line, the applied scale is from 1 to 5, in which 1 = very good
2 = good
3 = fair
4 = ⎫
5 = ⎭ inferior The table indicates that hair treated with the inventive compounds is imparted with improved combability, both in the wet and dry conditions. Moreover, the hair has improved handle or feel both in the wet and dry conditions. The gloss or shine of the dry hair is improved in one instance. It is clear from the table that hair treated with the inventive compounds becomes less heavy. This in turn means that there is a lesser deposit of compounds on the hair. On the other hand, if the deposit on the hair is too great, the hair obtains a fatty appearance and has to be frequently washed.

To summarize, the hair testing procedure was carried out with four creme rinses. The preparations I and II contain the inventive siloxanes A and B, while preparations III and IV contain the prior art siloxanes C and D corresponding to those disclosed in the Petzold patent. In the comparative testing, one of the inventive creme rinses was used with a non-inventive creme rinse. In so doing, preparations I and III on the one hand and preparations II and IV on the other hand were compared.

The preparations were used in such a manner that 10 test persons were selected, on whom one-half of the hair was treated with the inventive preparation while the other half of the same test person's hair was washed with the prior art product.

After the preparations had been used, the hair properties were ascertained. The evaluation scale extends from 1=very good to 5=inferior. An evaluation of the hair of the 10 test persons were taken and the total was then divided by 10. In this manner, the value, such as, for example, 1.7, was obtained.

The term "increase in heaviness" of the hair should be understood as follows: in the event that a preparation is not readily washed out from the hair, a film which has a tendency to build up on the hair surface after some time is composed of the absorbed substance. The hair then makes a fatty impression. Due to the deposit of the substance on the hair, the latter becomes heavier. What is desired, of course, is to have a creme rinse which causes as little "heaviness" as possible. In the above example, the "increase in heaviness" is graded or evaluated as follows:

1=desired low "heaviness"→5=undesired "heaviness".

What is claimed is:

1. A compound of the general formula

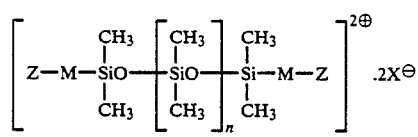

wherein Z is

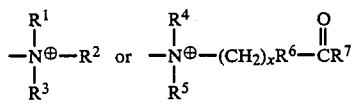

R¹, R², R³ are alkyl with 1 to 22 carbon atoms or alkenyl with 2 to 22 carbon atoms, at least one of the R¹, R² or R³ groups having at least 10 carbon atoms, R⁴, R⁵, R⁷ are alkyl with 1 to 22 carbon atoms or alkenyl with 2 to 22 carbon atoms, R⁶ is —O— or NR⁸, R⁸ being alkyl or hydroxyalkyl with 1 to 4 carbon atoms or hydrogen, x is 2 to 4, M is a bivalent hydrocarbon with at least 4 carbon atoms and having a hydroxyl group, n is a number from 1 to 200, and X⊖ is an inorganic or organic anion.

2. A compound as claimed in claim 1, wherein the bivalent hydrocarbon of M is interrupted by an oxygen atom.

3. A compound as claimed in claims 1 or 2, wherein R¹, R², R³, R⁴, R⁵ and R⁷ are the same or different in the molecule.

4. A compound as claimed in claims 1 or 2, wherein two of the groups R¹, R² and R³ are lower alkyl with 1 to 4 carbon atoms, while the third of said group is a long-chained hydrocarbon with at least 10 carbon atoms.

5. A compound as claimed in claim 4, wherein said long-chained hydrocarbon is saturated or unsaturated and is derived from naturally occurring fatty acids.

6. A compound as claimed in claims 1 or 2, wherein R⁴, R⁵ and R⁷ are situated next to each other in the molecule and R⁴ and R⁵ are lower hydrocarbons with 1 to 4 carbon atoms, while R⁷ is derived from a fatty acid R⁷COOH, which has at least 8 carbon atoms.

7. A compound as claimed in claims 1 or 2, wherein the two Z groups are the same or different in the molecule.

8. A compound as claimed in claims 1 or 2, wherein M is selected from the group consisting of

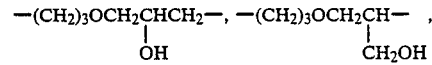

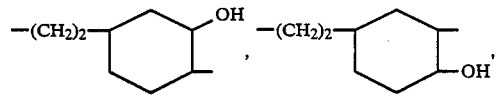

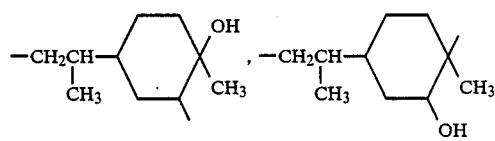

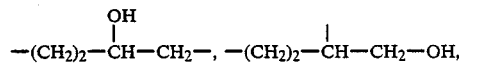

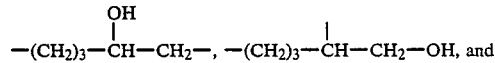

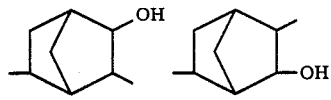

9. A compound as claimed in claims 1 or 2, wherein the compound is a mixture of compounds, the subscript n being an average value.

10. A compound as claimed in claims 1 or 2, wherein X⊖ is selected from the group consisting of acetate, chloride, bromine, hydrogen sulfate and sulfate ions.

11. A compound as claimed in claim 1, wherein n in the average molecule is from 5 to 50.

* * * * *